United States Patent [19]

Geis et al.

[11] Patent Number: 5,582,701
[45] Date of Patent: Dec. 10, 1996

[54] IONIC LIQUID-CHANNEL CHARGE-COUPLED DEVICE

[75] Inventors: Michael W. Geis, Acton, Mass.; Stephanie A. Gajar, Washington, D.C.; Nancy Geis, Acton, Mass.

[73] Assignee: Massachusetts Institute of Technology, Cambridge, Mass.

[21] Appl. No.: 360,260

[22] Filed: Dec. 20, 1994

Related U.S. Application Data

[62] Division of Ser. No. 134,965, Oct. 12, 1993, Pat. No. 5,374,834.

[51] Int. Cl.⁶ .......................... B01D 57/02; G01N 27/26
[52] U.S. Cl. .......................... 204/451; 204/453; 204/549; 204/550; 204/554; 204/556
[58] Field of Search .......................... 204/180.1, 183.1, 204/183.3, 186, 451, 452, 453, 549, 550, 554, 556

[56] References Cited

U.S. PATENT DOCUMENTS

| | | | |
|---|---|---|---|
| 3,686,088 | 8/1972 | Kashi | 204/550 |
| 4,390,403 | 6/1983 | Batchelder | 204/180.1 |
| 4,893,509 | 1/1990 | MacIver et al. | 73/517 AV |
| 4,900,414 | 2/1990 | Sibalis | 204/457 |
| 4,908,112 | 3/1990 | Pace | 204/299 R |
| 5,092,972 | 3/1992 | Ghowsi | 204/182.1 |
| 5,126,022 | 6/1992 | Soane et al. | 204/458 |
| 5,133,844 | 7/1992 | Stevens | 204/180.1 |
| 5,151,164 | 9/1992 | Blanchard et al. | 204/451 |

FOREIGN PATENT DOCUMENTS

| | | | |
|---|---|---|---|
| 0457748A1 | 11/1991 | European Pat. Off. | |
| 268877A1 | 6/1989 | German Dem. Rep. | B01D 57/02 |
| 2264783 | 9/1993 | United Kingdom | G01N 27/26 |

OTHER PUBLICATIONS

Lee et al. (1990) "Direct Control of the Electroosmosis in Capillary Zone Electrophoresis by Using an External Electric Field", *Anal. Chem.*, 62:1550–1552 month of publication not available.

Manz et al. (1992) "Planar Chips Technology for Miniaturization and Integration of Separation Techniques into Monitoring Systems" (Capillary Electrophoresis on a Chip), *J. Chromatog.*, 593:253–258 month of publication not available.

Li (1992) "Capillary Electrophoresis—principles, practice and applications", *J. Chromatog.*, 52:1–30, 55–139, 145–154, 398–540, 541–553 month of publication not available.

*Primary Examiner*—Bruce F. Bell
*Assistant Examiner*—William T. Leader
*Attorney, Agent, or Firm*—Thomas J. Engellenner; Anthony A. Laurentano; Lahive & Cockfield

[57] ABSTRACT

An ionic liquid-channel charge-coupled device that separates ions in a liquid sample according to ion mobility characteristics includes a channel having an inner wall that has a matrix liquid disposed within. An insulating material surrounds the channel, and an introduction element introduces a liquid sample into the channel. The sample is preferably a liquid solution that has at least one ionic specie present in the solution. The device further includes a gating element that establishes at least one charge packet in the channel in response to an externally applied input signal, and a transport element that induces the charge packet to migrate through the channel. The gate element can be a plurality of spaced-apart, electrically conductive, gate structures that are alternately disposable between a high voltage state and a low voltage state. The transport element further includes an application element that applies a variable voltage to the gating element. This application of voltage induces the charge packets to form under the gate structures and, when the voltage applied to an adjacent gate has a higher potential, induces the packet to migrate through the channel in that direction.

25 Claims, 4 Drawing Sheets

IONIC LIQUID-CHANNEL CHARGE-COUPLED DEVICE

This invention was made with government support under Contract No. F19628-90-C-002 awarded by the Air Force. The government has certain rights in the invention.

This is a divisional of application Ser. No. 08/134,965 filed on Oct. 12, 1993, now U.S. Pat. No. 5,374,834.

BACKGROUND OF THE INVENTION

This invention relates generally to charge coupled devices. More particularly, it relates to a monolithic ionic liquid-channel charge-coupled device (ILC-CCD) and methods of making the same.

The ability to quickly and to accurately analyze liquids to determine their constituents is of great general importance, and of particular importance in the biomedical research industries. Over the years, a variety of techniques have evolved that can analyze a solution and determine its component parts. These techniques can be divided into two basic categories. The first category includes fast and simple techniques, which detect only a few specific constituents. Devices which perform this technique include ion selectable electrodes, such as pH electrodes. A drawback of this general category is that, although the techniques are relatively fast and relatively simple to perform, they only detect specific sample constituents. Thus, a particular device is typically used to detect a relatively few, predetermined sample components.

The second category includes techniques which can be used to detect a broader range of constituents. Such techniques include ion mass spectrometers, gas chromatographs, and blood serum chemistry analyzers. A drawback of this general category is that the techniques require relatively large amounts of time and equipment to perform a complete analysis of the solution constituents. In addition, relatively large amounts of personnel, with their associated costs, are required to monitor and perform the analyses.

Some prior art techniques have sought to address the above problems by incorporating integrated circuit (IC) theory and technology into the device design and fabrication. IC technology has led to the development of smaller, more cost effective devices that are capable of detecting a broader range of constituents. Moreover, by incorporating IC technology, techniques can now be employed that incorporate previously inaccessible physical principles.

One such physical principle that would be beneficial in analyzing liquid samples is the physical principles employed by charge-coupled devices. Conventional charge coupled (CC) devices exist for generating a stream of electrons in response to an input signal, such as incident ambient light. Consequentially, CC devices are employed in many types of imaging devices, such as video recorders, camcorders, cameras and the like. Prior art CC devices usually consist of an array of polysiliconsilicon dioxide capacitors, typically mounted on a substrate. The substrate typically has a top face to which an insulating layer of silicon dioxide ($SiO_2$) is applied. A series of gate electrodes are then mounted to the silicon dioxide layer at various locations above the substrate. Each gate electrode has an associated electrical connector that communicates with an alternating current (AC) voltage source. The interface between the silicon dioxide layer and the substrate top face forms an electron channel. The channel defines the region in the CC device where electrons accumulate.

During operation of the CC device, a voltage is applied to each gate at a selected occurrence rate, called a stepping frequency. Typically, the electrons accumulate in packets under the gate electrode with the highest potential, e.g., most positive. The electron packets can be moved to the right or to the left of that gate by biasing the voltages positively on either adjacent gate, and biasing the gate above the packet negatively, such that the electrons move along the channel from regions of low potential to regions of high potentials.

There still exists a need in the art for improved analytical devices that can detect the components of a liquid solution. One particular advantageous device would employ the physical principles associated with CC devices. Additionally, a device that can relatively easily and relatively quickly determine all the ionized constituents of a liquid sample would present a major improvement in the art. Moreover, a device that is relatively easy to manufacture, that is relatively low-cost, and that is capable of detecting the presence of minute concentrations of a sample component would also present a major improvement in the art.

SUMMARY OF THE INVENTION

The foregoing objects are attained by the invention, which provides methods and apparatus for an ionic liquid-channel charge-coupled device that separates molecules in a liquid sample according to ion mobility characteristics. According to a preferred embodiment, the device includes a channel having an inner wall that has a matrix liquid disposed within. An insulating material surrounds the channel, and an introduction element introduces a liquid sample into the channel. The sample is preferably a liquid solution that has at least one ionic specie present in the solution. The device further includes a gating element that establishes at least one charge packet, e.g., a constellation of similarly charged ions, in the channel in response to an externally applied input signal, and a transport element that induces the charge packet to migrate through the channel.

The gate element can be a plurality of spaced-apart, electrically conductive, gate structures that are alternately disposable between a high voltage state and a low voltage state. The transport element further includes an application element that applies a variable voltage to the gating element. This application of voltage induces the charge packets to form under the gate structures and, when the voltage applied to an adjacent gate has a higher potential, induces the packet to migrate through the channel in that direction. One of the gates preferably applies a voltage to the insulating layer, which creates an electric field orthogonal to the channel, thereby repelling ions that may accumulate along the channel walls.

The channel can be coupled to a reservoir that functions as a storage receptacle for the matrix liquid and for the liquid sample. An electrode pad is preferably mounted in the reservoir and, in conjunction with a ground electrode which serves as a current return electrode, allows the application of a voltage across the length of the channel.

In another preferred embodiment of the invention, a detector element is disposed along the channel, which detects the presence of molecular and atomic species contained in the sample by measuring the changes in the conductivity of the channel as the species migrate across the detector.

According to another preferred embodiment, a device for separating molecular and atomic species in a matrix liquid can be fabricated by forming a first layer of a first insulating material upon a substrate, depositing a sacrificial structure of amorphous silicon upon the first insulating layer, and covering the structure with a layer of a second insulating material. An opening is then formed in the device and an etchant is introduced through the opening to remove the sacrificial structure, thereby forming a buried channel. A plurality of gate structures disposed at different locations along the channel receive an applied voltage from a voltage source. This applied voltage induces the molecular species to migrate from gate-to-gate along the channel. For example, molecular species accumulate under the gates with the highest potentials, and when an adjacent gate is biased more positively than the gate with the accumulated species, the species move in that direction. Hence, by biasing the adjacent electrodes either more positively or more negatively, the species can be moved to the right or to the left of that gate. Similarly, positively charged species will move to regions of the lowest potential.

In another preferred embodiment, before the sacrificial structure is deposited on the insulated substrate, a layer of the second insulating material is deposited over the insulated substrate. Similarly, before the opening is formed in the device, another layer of the first insulating material is deposited over the second insulating material. Preferably, the first insulating material is silicon dioxide; the second insulating material is silicon nitride; and the etchant is tetramethylammonium hydroxide.

The invention will next be described in connection with certain preferred embodiments. However, it should be clear that various changes and modifications can be made by those skilled in the art without departing from the spirit and scope of the invention. For example, various electronic detection units can be employed that detect the presence of various ionic species in a sample solution. Additionally, the device can be formed from any number or combination of insulating layers.

BRIEF DESCRIPTION OF THE DRAWINGS

The foregoing and other objects, features and advantages of the invention will be apparent from the following description and apparent from the accompanying drawings, in which like reference characters refer to the same parts throughout the different views. The drawings illustrate principles of the invention and, although not to scale, show relative dimensions.

DETAILED DESCRIPTION

Figure 1:
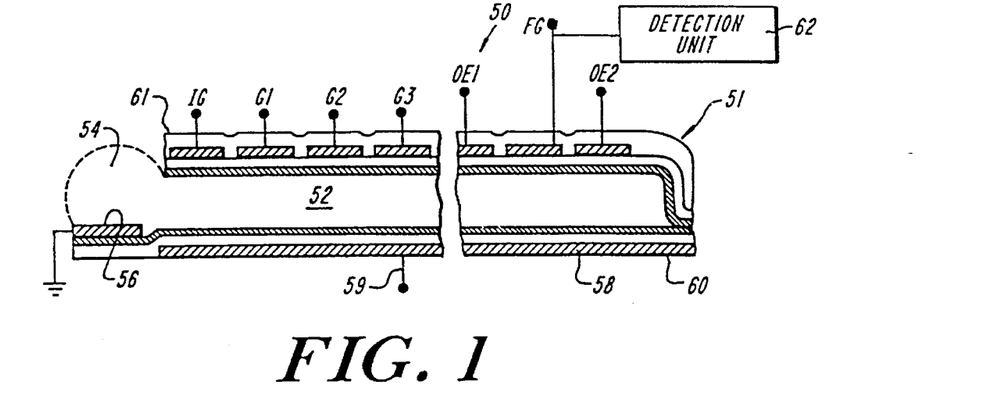
FIG. 1 is a cross-sectional view of an ILC-CCD according to a preferred embodiment of the invention.

FIG. 1. depicts an ionic liquid-channel charge coupled device 50 according to a preferred embodiment of the invention. The device 50 includes a housing 51 having a channel 52 that is fluidly coupled to an input reservoir 54, denoted by the black dashed lines. The reservoir 54 contains a matrix liquid (not shown) that functions as a background or transportation medium for various ionic species. The matrix solution can be any analytic solution such as water, and is preferably glycerol. An electrode pad 56 mounts in the reservoir 54 and is connected to ground. A counter electrode 58 mounts to the housing bottom 60, and extends, in a first orientation, in a generally horizontal direction substantially parallel to the channel 52. Formed along the housing top 61 is a series of gate electrodes designated as IG, G1, G2 . . . Gn, OE1, BE and FG. A detection unit 62 is capacitively coupled to the floating gate FG or directly to the channel 52.

Each gate electrode has an electrode contact mounted thereto that is in electrical communication with an alternating current voltage source (not shown). Likewise, the counter electrode 58 has an electrode contact 59 mounted thereto that communicates with the voltage source. Voltage sources suitable for use in the present invention are known in the art and commercially available.

A sample solution (not shown) containing various ionic species is introduced into the channel 52 through the reservoir 54. The sample can be introduced to the reservoir 54 by any suitable mechanical means. Preferably, the reservoir 54 is exposed to the ambient environment along a top portion thereof, thereby facilitating the introduction of both the matrix liquid and the sample solution into the channel 52.

The electrode contacts preferably have low resistance and low polarization voltage. In a particularly preferred embodiment, the contacts consist of an electrically conductive plating, e.g. silver or gold, disposed over an insulating material such as polymer. The housing 51 is preferably formed using silicon chip technology, as described in further detail below.

Figure 2A:
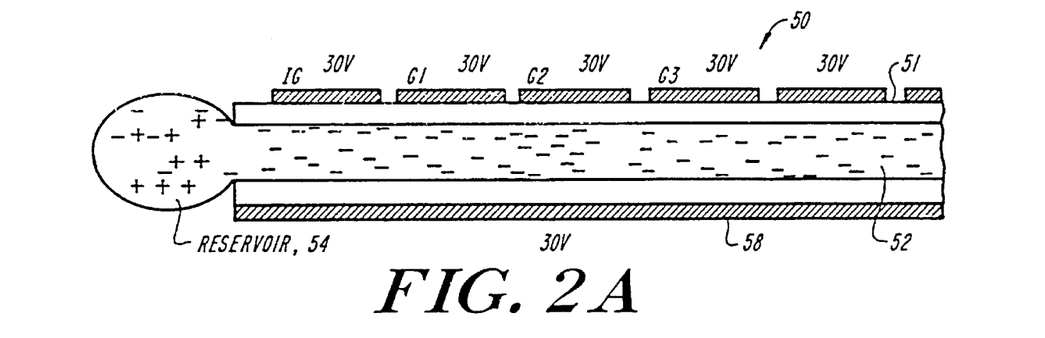
FIGS. 2a–2c show the migration of a packet of ions through the channel of the ILC-CCD of FIG. 1, according to a preferred practice of the invention.
Figure 2B:
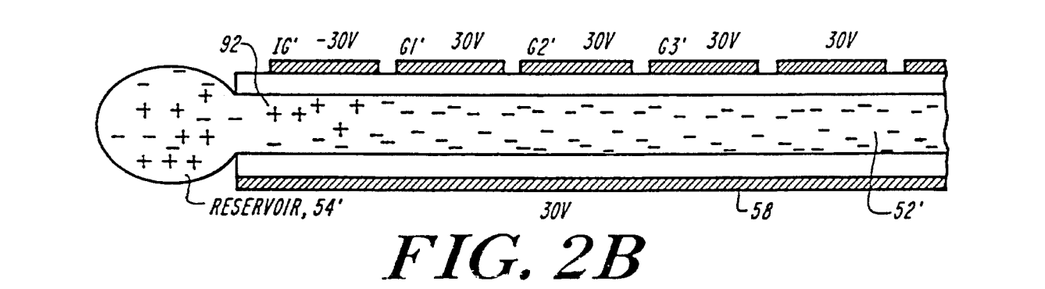
Figure 2C:
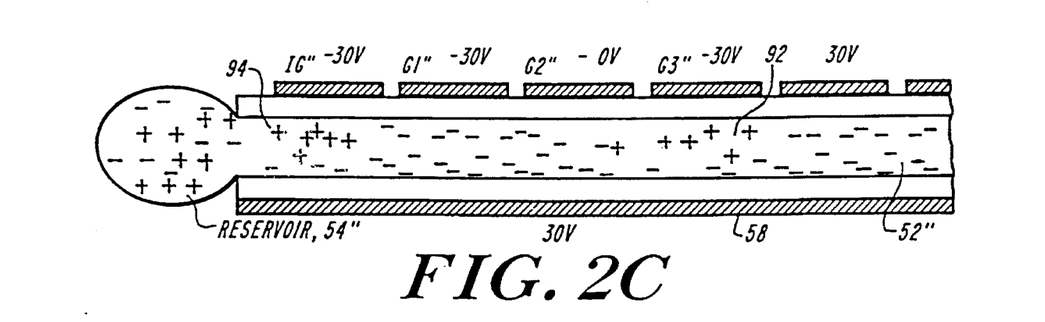

The device 50 separates ionic species contained in the liquid sample and held in the reservoir 54. As shown in FIG. 2, the device 50, prior to analyzing the sample constituents, clears the channel of either negatively or positively charged ions by biasing the gate electrodes and the counter electrode 58 either positively or negatively, respectively. As illustrated in FIG. 2a, the gates and counter electrode 58 are positively biased, effectively eliminating cations from the channel 52. Applying a potential lower than the originally applied potential on the input gate IG' adjacent the reservoir 54', forms a packet 92 of positively charged ions, as illustrated in FIGS. 2b and 2c. The packet 92 can be moved through the channel 52' and 52" towards the end opposite the reservoir (output end) by negatively biasing adjacent gates G1', G2', G3' . . . Gn in succession, thereby producing an ion current to the right. FIG. 2c shows the ion packet 92 when stepped three gate electrodes to the right, as well as the formation of a new ion packet 94 under the input gate IG". This method of transfer creates a "shifting staircase" potential profile under the gates, see FIG. 5. Those of ordinary skill will recognize that by biasing the input gate IG positive, the ion current density in the channel is correspondingly reduced since no new similarly charged ions diffuse into the channel 52.

Once a packet of ions is formed in the channel, the ion constituents separate in the channel according to their diffusion coefficients. For example, ions having relatively low diffusion coefficients have migration velocities lower than ions having relatively high diffusion coefficients. The ions with low diffusion coefficients migrate between the regions between adjacent gate electrodes slower than ions with higher diffusion coefficients. The voltages applied to the counter electrode 58 and to the gate electrodes also creates an orthogonal electric field which further induces the ions to migrate through the channel 52. As a result, the ion packet separates into constituent parts as the packet migrates from gate-to-gate along the channel. The voltages applied to the gates operate at a frequency called the stepping frequency which is defined as the number of voltage changes per second. At times, the stepping frequency operates at a sufficiently high frequency such that ions with a low diffusion coefficient are prevented from traveling forward (away from the reservoir), thus becoming essentially immobilized. Accordingly, since the voltages applied to the gate electrodes are not inducing the ions to migrate through the channel, the ion current for that particular constituent decreases along the length of the channel.

In a preferred embodiment, a suitable voltage is applied to a selected gate electrode to repels ions that cohere to the channel walls. During typical applications, the externally applied orthogonal electric field created by the applied voltage repels these ions from the channel wall. These ions interact with the ionic species migrating through the channel 52 that are adjacent to the channel wall. As a result, the ions concentrated towards the center of the capillary travel at a velocity faster than the ions along the wall surface, since the ions along the wall surface interfere with and ultimately decrease the migration velocity of ions traveling close to the channel wall.

The output electrodes OE1 and OE2 located at the end of the channel 52 generate a potential well that allows ions traveling through the channel to accumulate at the output end. Preferably, the output electrodes are biased at a constant voltage level to maintain a constant potential well. The floating gate FG capacitively couples the device 50 to the detection unit 62, as described further below.

Figure 3:
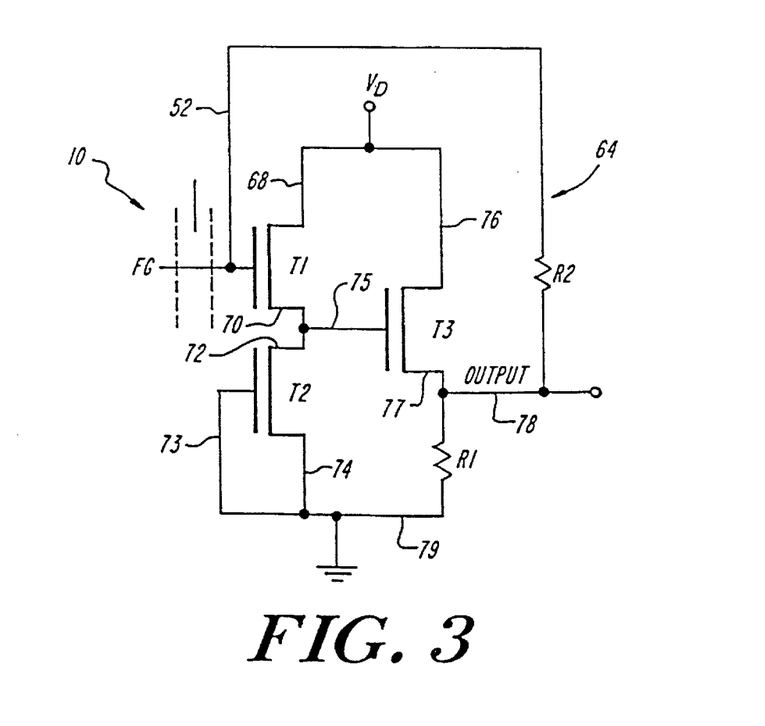
FIG. 3 is a schematic circuit diagram of a preferred detection circuit used in conjunction with the ILC-CCD of FIG. 1.

The detection unit 62 includes a detection circuit 64, as shown in FIG. 3. The circuit 64 is a two-stage amplifier that includes feedback resistor R2, and current sensing resistor R1. Transistor T1 is preferably a floating gate MOSFET that is capacitively coupled to the floating gate electrode FG, and hence the channel 52. The transistor drain 68 is coupled to a source voltage $V_D$, and the transistor drain 70 is connected to the drain 72 of transistor T2 and to the gate 75 of transistor T3. Both the gate 73 and source 74 of transistor T2 are connected to ground. By grounding the gate 73 of transistor T2, the gate to source voltage is pulled to zero, forcing the transistor to operate in the pinch-off region and effectively transforming the transistor T2 into a load resistance. The drain 76 of transistor T3 is connected to voltage source $V_D$, and the source transistor 77 is connected to one end of the current sensing resistor R1. The opposite end of the resistor R2 is connected to ground, and the output voltage 78 is measured across the resistor R.

The feedback resistor R2 incorporates the signal from the source 77 of transistor T3 to the gate 66 of transistor T1. The resistor R1 ensures that the transistor T1 is biased in the active region. The impedance value of resistor R1 is chosen such that the time constant of the capacitance of channel 52 and the resistor R1 is much larger than the externally applied stepping frequencies. In other embodiments, the resistor R1 can be replaced with a switch which shorts in the channel 52.

Again, with reference to FIG. 3, when no ion packet is positioned beneath the floating gate FG that is capacitively coupled to transistor T1, no ion current is present to change the potential at the gate 66 of T1, and the current through T1 does not change. As a result, the output voltage measured across resistor R1 remains essentially the same. When an ion packet is positioned beneath the floating gate FG by manipulating the adjacent gate voltages, the ion packet changes the floating gate potential, which modulates the current at the gate 66 of transistor T1, thereby charging the current through T1. The drain current change flowing from the drain 76 to the source 77 of transistor T3 creates an output voltage change across resistor R2. This output voltage can be connected to a variety of display apparatuses, such as digital display units, LED read-outs and the like.

Alternatively, the detector can be an dement that responds to changes in the channel 52 through capacitive coupling or the like.

In a preferred embodiment, the device 50 includes between 600 and 1000 gate electrodes that extend along the length of the channel 52. The dimensions of the channel 52, when fabricated, are preferably between 10 and 500 nm high (equal to or less than the Debye length of the liquid matrix), between 1 and 10 µm wide, and between 0.3 and 5.0 mm long.

Figure 4:
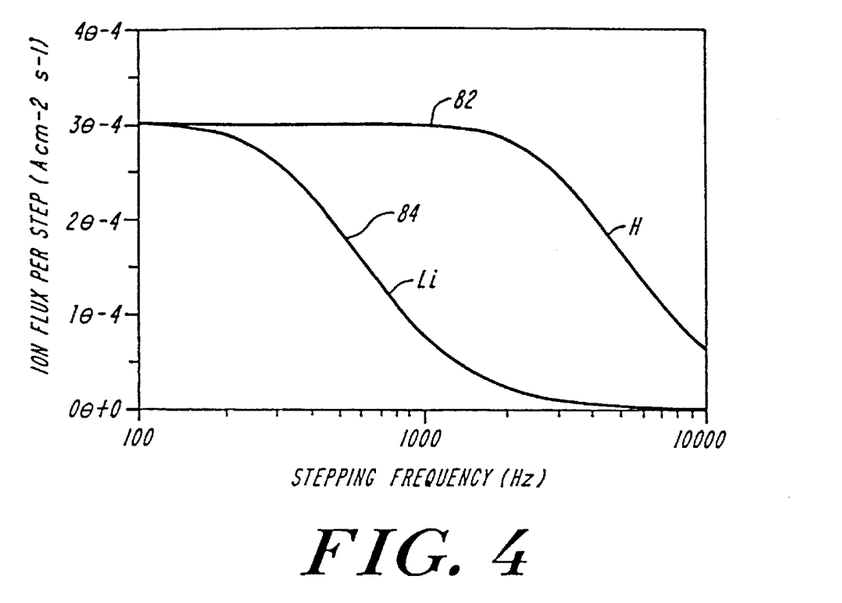
FIG. 4 is a graph comparing the channel ion flux as a function of stepping frequency for two selected ions.
Figure 5A:
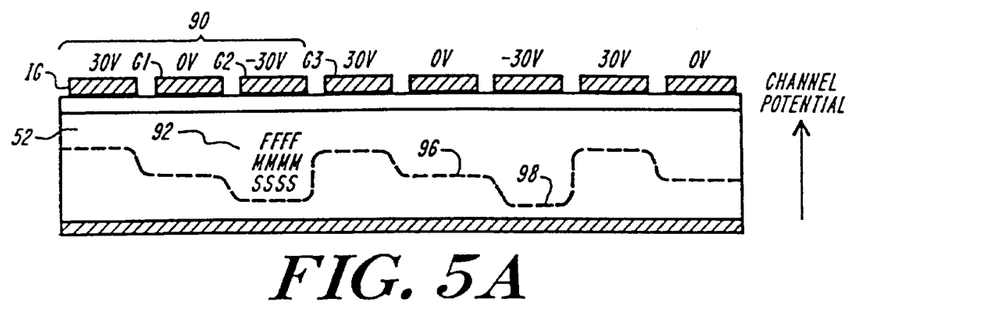
FIG. 5a–5d shows the separation of ions in the channel of the ILC-CCD of FIG. 2, according to a preferred practice of the invention.
Figure 5B:
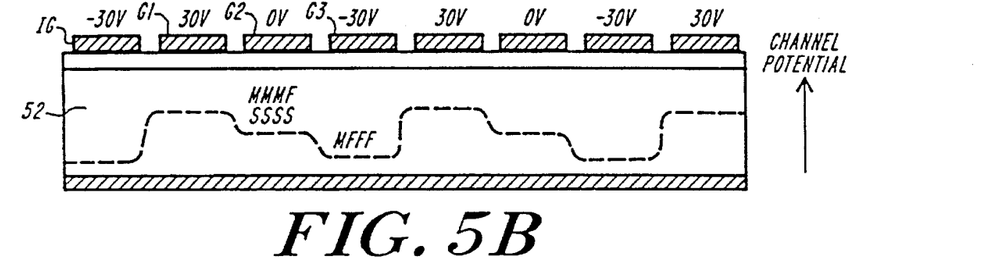
Figure 5C:
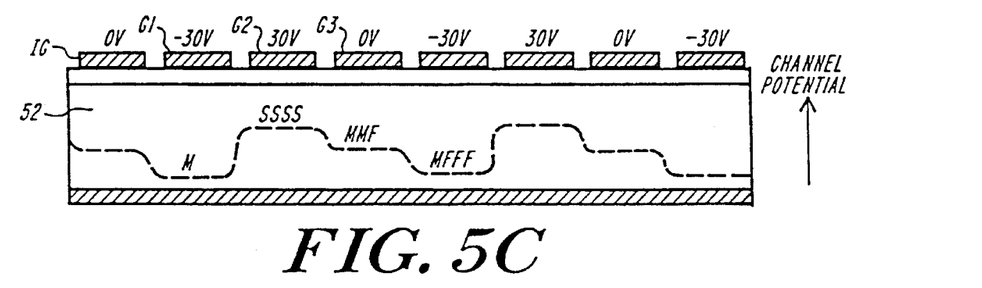
Figure 5D:
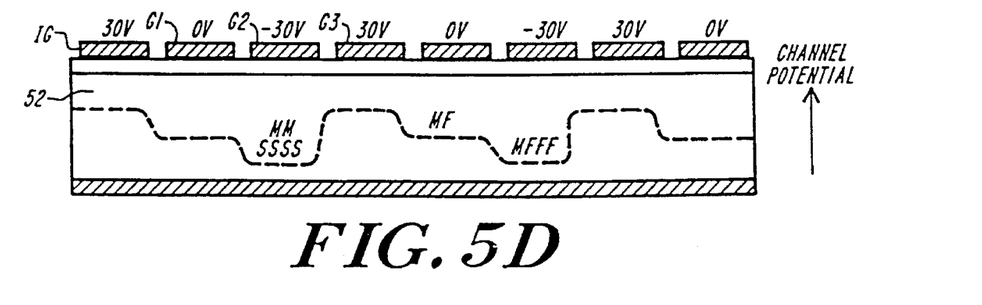

The ion separating ability of the present invention is exemplified by the graph depicted in FIG. 4, which shows a comparison of the ion current (measured as the ion flux per step) in the channel 52 for two selected constituents ($Li^+$ ions and $H^+$ ions) having substantially different diffusion coefficients. The ion currents are measured over a range of stepping frequencies, and are logarithmically graphed for comparison purposes. As illustrated, at relatively low stepping frequencies, the $H^+$ ion concentration 82 and the $Li^+$ ion concentration 84 are essentially equal. The device 50, therefore, induces the ions to travel through the channel at approximately the same velocity, despite the differences in diffusivity. However, as the frequency increases, the channel 52 develops a substantially $H^+$ ion current and a substantially reduced $Li^+$ ion current. At still higher frequencies, the $Li^+$ ion current reduces to near zero. The $Li^+$ ion current decreases with increasing stepping frequency since the gate electrodes along the channel switch at a selected rate which first impedes the forward progress of the ions, and then eventually reverses the migration direction of the ions. The dynamics of this ion migration and separation are depicted in FIG. 5.

FIG. 5 shows the separation of ions in the channel 52 as an ion packet 92 is transferred through the channel 52 by varying the stepping frequency of adjacent gate electrodes IG, G1, G2, G3 . . . Gn. The shifting staircase potential produced by the stepping frequency forms potential wells 96 and 98 that can be repeated by varying the gate electrode voltages in a selected sequence. The dashed line represents the zero potential locations in the channel 52. In a preferred embodiment, the potential at the gate electrodes are repeated every three gates, where each set of three gates is called a cell 90. As illustrated, the ion packet 92 includes ions having different diffusion coefficients, designated as fast ions F, slow ions S, and medium ions M. During a selected cycle, the ion packet 92 constituents separate as they are transferred through the channel 52. When the stepping frequency of the cycle is high enough, the fast ions F travel forward, while the slow ions S remain essentially stationary. Some of the ions with a relatively medium diffusion coefficient M travel forward, while others remain substantially stationary. It will be readily apparent to those skilled in the art that the gate electrodes can be biased so as to cause the ions to travel back into the reservoir (to the left), such that no ion current is generated for any particular ionic species.

It is a significant feature of the ILC-CCD device of the present invention that constituents of an ion packet can be separated despite having diffusion coefficients within a narrow band, and without suffering a corresponding loss in ion resolution. The ion packet constituents can be separated by operating the device 50 at different frequencies, and preferably at three different frequencies. A preferred method is to clock the CC device 50 back at frequency f1 for N1 periods, forward at frequency f2 for N2 periods, and then back again at frequency f3 for N3 periods. When the frequencies and the time periods are properly adjusted, a net forward ion flux is created for a window of diffusivity. The net forward ion flux accumulates ions, e.g., cations, at the output gate electrodes OE1 and OE2 after each cell cycle. The ions continue to accumulate at the output until the back diffusion flux of ions equals the net forward ion flux, e.g., pumping flux. Thus, for ions within this window of diffusivity, their concentration increases along the length of the channel, while all other ions decrease to zero.

Figure 6:
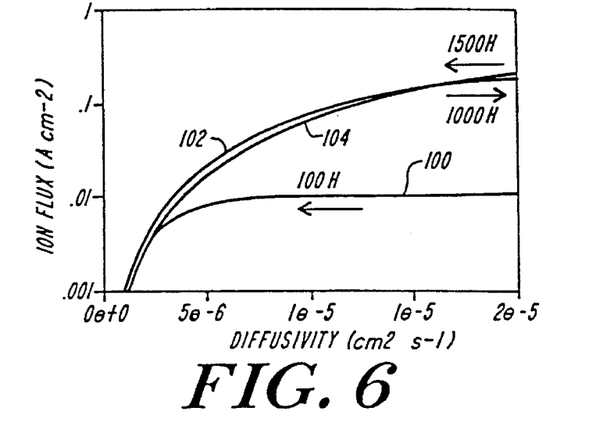
FIG. 6 is a graph illustrating the quantity of ion current generated in the ILC-CCD of FIG. 1 as a function of both stepping frequency and diffusivity.
Figure 7:
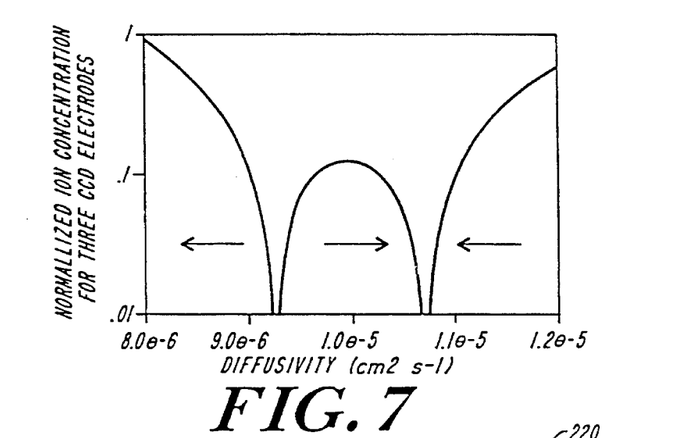
FIG. 7 is a graphical illustration of the ion separating feature of the ILC-CCD according to a preferred practice of the invention.

FIGS. 6 and 7 graphically illustrate the above "frequency sweeping" method where the ILC-CCD with elements 1 μm in length is repeatedly operated at three different frequencies. By way of example, the ILC-CCD 50 is first operated at a frequency of 100 Hz at 10 clock periods in such a manner as to produce a net ion current back into the reservoir 54, pumping virtually all cations backward. The device is then clocked forward at a frequency of 1000 Hz for 100 clock periods, which produces a net forward ion current out of the reservoir. The ion packet constituents include ions having relatively medium and relatively fast diffusion coefficients. Then at the highest frequency of 1500 Hz, the device is again clocked backwards 112 cell periods, pumping the fastest ions backward in the channel 52. The process is then continually repeated. FIG. 7 compares the ion concentration in the channel against the diffusion coefficients of the ions during the frequency sweeping method. At 100 Hz, there is only a net concentration in the channel of ions with diffusion coefficients above $5 \times 10^{-6}$, as illustrated by line 100. The bold arrow represents the direction the device 50 was clocked during this process. At the intermediate frequency of 1000 Hz, with the device now clocked forward, the ion flux increases with the diffusion coefficient, as shown by line 102. Similarly, when the device is clocked at the highest frequency of 1500 Hz, the ion flux also increases with increasing ion diffusivity, as shown by line 104, despite the ions being pumped backwards. The net pumping flux for the three frequency sequence is the weighted sum of the individual fluxes produced by each of the three frequency operations. The fluxes are weighted according to the number of clock periods in which the frequency operates. Thus, a cation with a particular diffusion coefficient, e.g., $1 \times 10^{-5}$ cm$^2$/s, accumulates at the output of the device, while the ions with higher and lower diffusion coefficients are pumped back into the reservoir. The ability to separate and concentrate at the output of the device different ions having different diffusion coefficients within a narrow range, allows for the detection and identification of extremely small amounts of ions. Those skilled in the art will also recognize that the frequency sweeping can occur in the reverse direction.

FIG. 7 graphically illustrates the ability of the present invention to identify constituents of a sample solution that are within a relatively narrow window of diffusion coefficients. The device 50 (as shown in FIG. 2) pumps ions present in the channel 52 to the right, until the ion concentration at the left (near the reservoir 54) of the channel 52 increases to where diffusion of ions back towards the reservoir from the output end of the channel equals the pumping current. By employing the abovementioned stepping frequencies and clock periods, the maximum concentration of ions at the channel output occurs at a diffusivity of $1 \times 10^{-5}$ cm$^2$/s, indicated by bold arrow 114. At this diffusivity, there is approximately a 10% increase in the ion concentration between each gate electrode at the output end of the channel. Ions having diffusivity levels approximately 10% higher or lower than the ion having a diffusivity of $1 \times 10^{-5}$ cm$^2$/s are pumped back towards the reservoir, and eliminated from the channel 52. The bold arrows 110 and 112 show the forced migration of ions with difference diffusivities back towards the reservoir 54. By varying the stepping frequency of the gate electrodes, different ions can be concentrated at the output end. This significant feature allows the ILC-CCD to reject alias compounds that have diffusion coefficients substantially similar to that of a desired analyte. The increasing ion concentration along the length of the channel, in conjunction with the ion separation that occurs, allows the detection unit 62 to detect and identify a particular ion within the range of coefficients, which would otherwise be undetectable without this concentrating ability.

In accordance with the present inventive device, ions accumulate in the potential well formed beneath the output electrode, prior to transfer between the output electrodes. By way of example, and referring to FIGS. 2 and 6, ions accumulate beneath output electrode OE1 prior to transferring the ions to the adjacent electrode OE2. Accumulating the ions in a parcel beneath the electrode OE1 and then expeditiously transferring the parcel to the adjacent output electrode OE2, by biasing the electrode OE2 more negatively, avoids individually pulling the ions across the region between the two electrodes over a longer period of time. An advantage of this approach is that it effectively eliminates low frequency noise problems that are characteristic of charge-coupled devices and detection circuits when operating at these lower frequencies. This advantage manifests itself in better sensitivity to very low ion concentrations by virtually eliminating the problem of "popcorn" and 1/f voltage noise.

Figure 8:
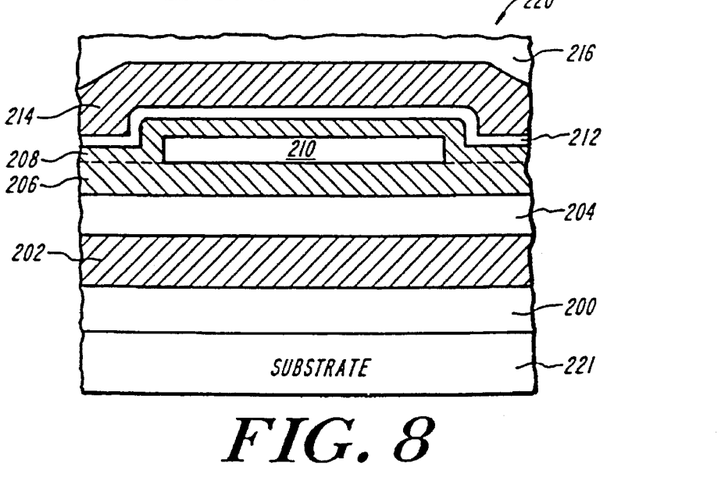
FIG. 8 is an orthogonal cross-section of the ILC-CCD of FIG. 1 illustrating the different material layers of the device according to a preferred embodiment of the invention.

FIG. 8 illustrates the various layers and materials that are utilized to form the housing 51 of the device 50 of the present invention. The housing is formed by depositing a layer of polysilicon 202, preferably phosphorus-doped, over the substrate 221 by a fabrication technique, such as chemical vapor deposition. The layer 202 preferably forms the counter electrode 58, and the substrate is preferably a semiconductor wafer. The polysilicon layer is electrically and ionically insulated from the matrix liquid and the sample solution by a layer of electrically insulating material 204, and a layer of silicon nitride (Si$_3$N$_4$) 206, which is also deposited on the insulating material 204 by chemical vapor deposition or like techniques. Both layers have a thickness of 50 nm. The substrate is preferably insulated from the polysilicon layer 202 by insulator 200, which is preferably a 2 μm thick layer of silicon dioxide.

A sacrificial structure 210, such as amorphous silicon, is positioned on the silicon nitride layer 206. If more than one channel is desired, then a series of sacrificial structures can be placed along the layer 206. A second layer 208 of silicon nitride is formed over the structure 210, and a second layer of insulating material 212 is deposited over the silicon nitride layer 208. The silicon nitride layers 206 and 208 form the upper and lower halves of the channel 50. Again, a layer of polysilicon 214 is deposited on the insulating layer 212, and is patterned to form the gate electrodes IG, G1, G2, G3 . . . Gn. Finally, a third encapsulation layer of the silicon dioxide 216, is deposited over the gate electrodes.

The channel 52 is created by aperturing the assembly 220 to form an opening (not shown) that communicates with the sacrificial structure 210. An etchant, preferably tetramethylammonium hydroxide, is introduced through the opening and completely removes the structure 210 to form the channel 52, without harming the silicon nitride layers 206 and 208.

The channel 52 formed in the assembly 220 is preferably elongate in shape. However, whenever it is desired that the overall length of the channel exceed the diameter of the silicon wafer, the channel length can be increased by forming the sacrificial structure in a serpentine, spiral, or other like configuration.

Another advantage of the present invention is the low voltage levels required to facilitate separation of the ion packet into constituent parts. Low voltage levels can be employed by the device 50 since the gate electrodes are spaced relatively close together. In a preferred embodiment of the invention, the voltage difference between adjacent gate electrodes is preferably between 5 V and 60 V, and more preferably, 20 V. The separation between adjacent electrodes is preferably between 0.1 µm and 10 µm, and more preferably about 1 µm. The gate length is preferably between 0.1 µm and 50 µm, and more preferably about 1 µm.

Having described the invention, what is claimed as new and desired to be secured by Letters Patent is:

1. A method of separating an ionic constituent of a liquid comprising the steps of:

introducing a liquid into a charge coupled device having a channel extending along a longitudinal axis, said charge coupled device having a plurality of gate electrodes coupled to one side of the channel at locations spaced-apart along said axis, such that upon application of a voltage to one or more gate electrodes an electric field is established within the channel in the vicinity of the gate electrode, applying a voltage to at least one of said gate electrodes to induce an ionic constituent of said liquid to accumulate in the vicinity of said gate electrode, and applying a voltage to at least a second one of said plurality of gate electrodes spaced along said axis to induce said ionic constituent to migrate along said channel, such that said constituent is separated from other components of said liquid during the induced migration.

2. The method of claim 1 wherein the step of applying a voltage to said second gate electrode further comprises applying said voltage for a sufficient time and at a sufficient potential to induce said constituent to migrate as an ion packet.

3. The method of claim 1 wherein the method further comprises the step of applying a voltage to yet another one of said plurality of gate electrodes such that the constituent is induced to migrate from gate-to-gate in a selected direction and at a defined rate.

4. The method of claim 1 wherein the voltage applied to the gate electrode is a variable voltage.

5. The method of claim 4 wherein the method further comprises applying said variable voltage to a series of said plurality of gate electrodes sequentially to establish a selected stepping frequency whereby only a selected ionic constituent of said liquid migrates within said channel.

6. The method of claim 5 wherein the method further comprises establishing a first stepping frequency to induce migration of said constituents in a first pattern, and then establishing a second stepping frequency to induce migration of said constituent in another pattern, such that separation of said constituent is achieved by net migration differences.

7. The method of claim 6 wherein establishing said second stepping frequency drives said constituent in said channel in a direction opposite to the direction of said first stepping frequency.

8. A method for separating ionic constituents of a liquid, comprising the steps of providing a charge coupled device having a channel extending along a longitudinal axis and having a plurality of gate electrodes coupled to one side of the channel at locations axially spaced-apart along said axis, introducing a liquid having at least one ionic constituent to said channel, applying to each one of at least two of said plurality of gate electrodes a selected voltage to induce said constituent to migrate in said channel, such that said induced migration separates said constituent from other ionic components of said liquid.

9. The method of claim 8 wherein the step of applying said voltage to each one of said gate electrodes forms an ion packet in said channel that migrates at least partly therethrough, said ion packet including at least two ionic constituents each having a selected diffusion coefficient, wherein the constituents of said ion packet separate from each other according to said diffusion coefficients.

10. The method of claim 8 wherein the step of applying said voltage to each one of said gate electrodes separates a selected ionic constituent from said other components of said liquid.

11. The method of claim 8 wherein the step of applying a voltage to at least two of said plurality of gate electrodes comprises the step of applying to a first gate electrode a first selected voltage to form a an ion packet, and applying to a second axially spaced-apart gate electrode a second voltage to induce the ion packet to migrate thereto.

12. The method of claim 8 wherein the method further comprises applying sequentially a second voltage to at least a portion of said gate electrodes to induce said migration of said ionic constituent and to further separate said ionic constituent from said other liquid components.

13. The method of claim 12 wherein the method further comprises applying sequentially a third voltage to at least a portion of said gate electrodes further inducing migration and separation of said ionic constituent from said other components in said channel.

14. The method of claim 8 wherein said step of applying said voltage comprises the step of applying sequentially a plurality of voltages each having a different frequency to at least a portion of said gate electrodes to produce a net forward migration of said ionic constituent in said channel.

15. A method for separating at least one selected ionic constituent of a liquid in a charge-coupled device, comprising the steps of providing a charge-coupled device having a channel extending along a longitudinal axis and having a plurality of gate electrodes coupled to one side of the channel at locations axially spaced along said axis, and applying a selected voltage to at least a portion of said gate electrodes to induce said ionic constituent of said liquid to migrate along said channel, such that said constituent of said liquid separates from other liquid components during said induced migration according to at least a diffusion coefficient of said constituent.

16. A method for separating ionic constituents of a liquid, comprising the steps of providing a charge-coupled device having a channel extending along an axis with a defined length, and a plurality of gate electrodes coupled to one portion of the channel at locations axially spaced along said axis, and applying to at least one of said plurality of gate electrodes a first voltage having a first selected frequency, thereby inducing the ionic constituents present in the liquid to migrate along the channel in a first direction, whereby said induced migration of said constituents separates one or more ionic constituents along said channel.

17. The method of claim 16 further comprising the step of applying sequentially to at least one of the gate electrodes a second voltage having a second selected frequency f2, thereby inducing at least one selected ionic constituent present in the liquid to migrate at a different rate.

18. The method of claim 17, wherein each ionic constituent of the liquid has a selected diffusion coefficient, further comprising the step of applying sequentially to at least one of the gate electrodes a third voltage having a third selected frequency f3, thereby further inducing said at least one selected ionic constituent to migrate at a different rate, such that said constituents of the liquid further separate along said channel according to said diffusion coefficients thereof.

19. The method of claim 18 wherein the first frequency f1 is less than the frequency f2, and the frequency f2 is less than the frequency f3.

20. The method of claim 18 wherein the first selected frequency f1 is applied for a selected period N1, said second frequency is applied for a selected period N2, and said third frequency f3 is applied for a selected frequency N3, wherein the number of periods N1 is less than the number of periods N2, and the number of periods N2 is less than the number of periods N3.

21. The method of claim 18 wherein the first frequency f1 is greater than the frequency f2, and the frequency f2 is greater than the frequency f3.

22. The method of claim 16 further comprising the step of applying sequentially to at least one of the gate electrodes a second voltage having a second selected frequency f2, thereby inducing at least one selected ionic constituent present in the liquid to migrate in a different direction.

23. The method of claim 16 further comprising the step of applying sequentially to at least one of the gate electrodes a second voltage having a second selected frequency f2, thereby inducing at least one selected ionic constituent present in the liquid to migrate in said first direction.

24. The method of claim 16, wherein each ionic constituent of the liquid has a selected diffusion coefficient, further comprising the steps of applying sequentially to at least one of the gate electrodes of the charge coupled device a second voltage having a second selected frequency, thereby inducing selected ionic constituents present in the liquid to further migrate along said channel according to said diffusion coefficient in said first direction, applying sequentially to at least one of the gate electrodes of the charge coupled device a third voltage having a third selected frequency, and detecting at least one of said ionic constituents migrating along said channel.

25. A method for separating ionic constituents in a liquid, wherein each constituent has a selected diffusion coefficient, the method comprising the steps of:

providing a charge coupled device having a channel extending along a longitudinal axis and a plurality of gate electrodes coupled to one side of the channel at locations axially spaced apart along said axis, applying to at least one of said gate electrodes a first selected voltage having a first selected stepping frequency, such that at least a portion of said constituents present in the liquid are induced to migrate along said channel in a first direction, applying to at least one of said gate electrodes a second variable voltage having a second selected stepping frequency for inducing at least a portion of said constituents having diffusion coefficients within a selected range to migrate along the channel in said first direction, wherein said induced migration caused by said first and second variable voltages and stepping frequencies separates one or more constituents along the length of the channel according to said diffusion coefficients.

\* \* \* \* \*